United States Patent
King et al.

(10) Patent No.: US 6,491,273 B2
(45) Date of Patent: Dec. 10, 2002

(54) RELEASABLE LOCKABLE RE-POSITIONABLE ARM-LIKE SUPPORT APPARATUS

(75) Inventors: Brent W. King, Calgary (CA); Geof F. Auchinleck, Vancouver (CA); Ken W. Moore, Calgary (CA)

(73) Assignee: Tenet Medical Engineering Inc., Calgary (CA)

( * ) Notice: Subject to any disclaimer, the term of this patent is extended or adjusted under 35 U.S.C. 154(b) by 90 days.

(21) Appl. No.: 09/741,870

(22) Filed: Dec. 22, 2000

(65) Prior Publication Data

US 2002/0014567 A1 Feb. 7, 2002

(30) Foreign Application Priority Data

Jul. 28, 2000 (CA) ............................................. 2314758

(51) Int. Cl.⁷ ................................................. E04G 3/00
(52) U.S. Cl. .............................. 248/276.1; 248/288.51; 403/90
(58) Field of Search ......................... 248/276.1, 288.31, 248/280.11, 292.13, 288.51, 274.1, 159, 160; 269/74; D24/133, 140; 403/90, 83, 91, 92

(56) References Cited

U.S. PATENT DOCUMENTS

| | | | | |
|---|---|---|---|---|
| 3,278,207 A | * | 10/1966 | Barish et al. ............... 285/312 |
| 3,638,973 A | * | 2/1972 | Poletti ......................... 137/583 |
| 3,986,692 A | * | 10/1976 | Kinoshita ................... 248/160 |
| 4,149,384 A | * | 4/1979 | Marshall ....................... 60/542 |
| 4,767,231 A | * | 8/1988 | Wallis ........................ 248/276.1 |
| 4,807,618 A | * | 2/1989 | Auchinleck et al. ......... 128/878 |
| 4,817,592 A | * | 4/1989 | Auchinleck et al. ......... 128/855 |
| 5,010,900 A | * | 4/1991 | Auchinleck et al. ......... 128/855 |
| 5,020,933 A | * | 6/1991 | Salvestro et al. ............. 403/24 |
| 5,104,103 A | * | 4/1992 | Auchinleck et al. ......... 128/878 |
| 5,289,948 A | * | 3/1994 | Moss et al. ................... 222/135 |
| 5,348,259 A | * | 9/1994 | Blanco et al. ................. 227/19 |
| 5,609,565 A | * | 3/1997 | Nakamura ................ 248/278.1 |
| 5,918,844 A | * | 7/1999 | Ognier ....................... 248/276.1 |
| 6,371,425 B2 | * | 4/2002 | Fidler ........................ 248/181.1 |
| 6,379,073 B1 | * | 4/2002 | Yoo et al. ............... 248/288.31 |
| 2002/0000503 A1 | * | 1/2002 | Fidler .................... 248/288.51 |

* cited by examiner

Primary Examiner—Kimberly Wood
Assistant Examiner—Naschica S. Morrison
(74) Attorney, Agent, or Firm—Blake, Cassels & Graydon LLP; Terry L. Leier

(57) ABSTRACT

Discloses a multi-joint arm-like support including a mount connecting to an elongate first limb section by a paired ball-and-socket joint, or shoulder joint. The first limb section is connected to a second limb section by a rotatable joint or elbow joint. The second limb section has a ball-and-socket joint connecting to an instrument mount. The joints include fluid activated locks to enable the arm to be freely moveable when the fluid activated locks are released and locked in position when the fluid activated locks are activated.

8 Claims, 5 Drawing Sheets

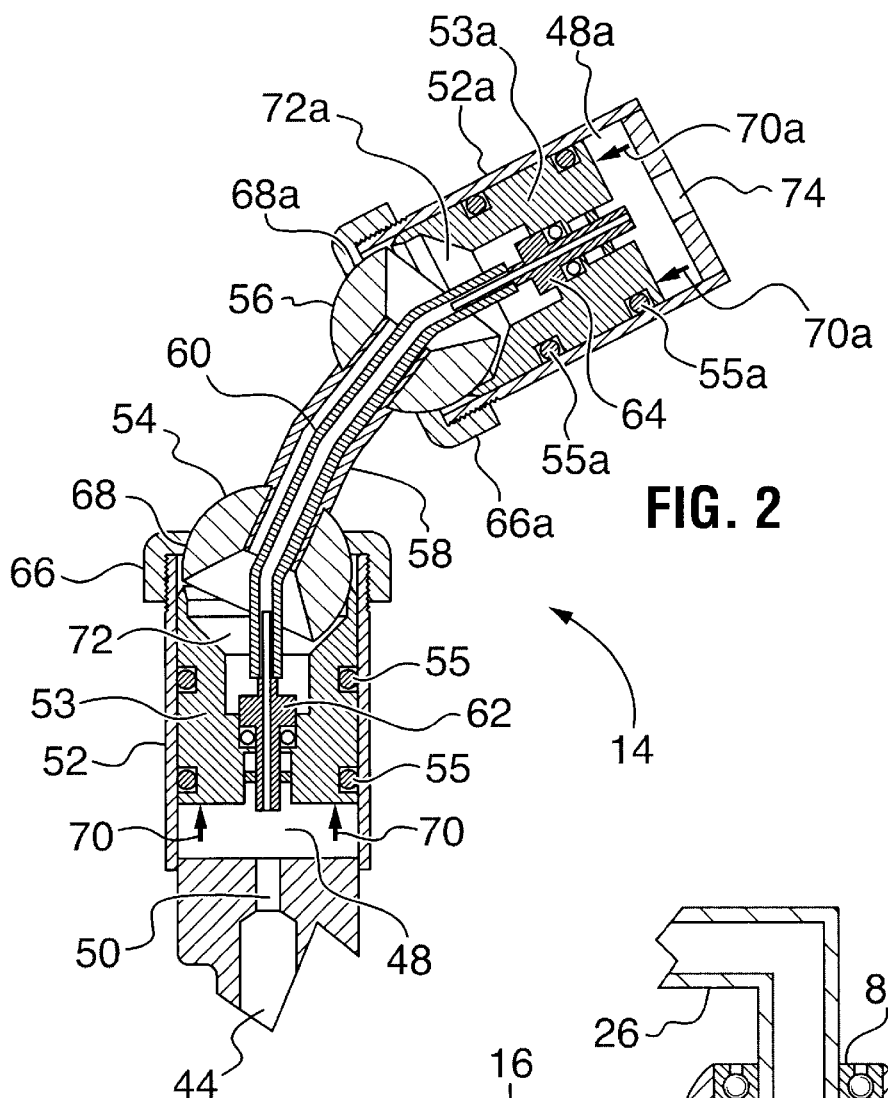
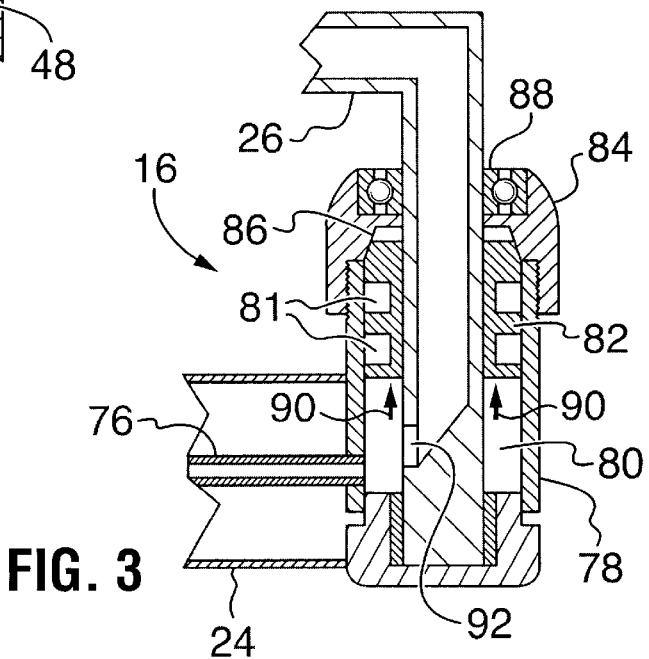

RELEASABLE LOCKABLE RE-POSITIONABLE ARM-LIKE SUPPORT APPARATUS

FIELD OF THE INVENTION

This invention relates to lockable support apparatus and more particularly to a multi-joint adjustable, lockable arm-like support capable of holding tools, instruments and the like.

BACKGROUND TO THE INVENTION

Frequently certain surgical procedures make it necessary to hold a patient's body or a limb in a certain orientation or in a series of orientations that are to be fixed and maintained for extended periods, such as for example to perform orthopaedic surgery on a joint such as a shoulder or knee joint.

Surgical instruments have been developed that operate in co-operation with fibre optical equipment to perform surgical procedures and carry out surgical intervention with the benefit of small incisions or punctures to gain access to internal body tissues and structures to effect the surgical intervention. Use of such surgical instruments and fibre optic equipment presents the need for manipulation and holding of several instruments to effect the surgical procedure. Even a single instrument may be provided with several controls which require manual manipulation resulting in the need for additional staff or devices to hold the instrument or instruments during the course of the surgical procedure.

For example, U.S. Pat. No. 5,918,844 to Ognier describes a support device for a medical or surgical instrument which is adapted for use in holding instruments during surgery. Heretofore available apparatus, such as that taught by Ognier for example, has limitations of positioning and placement that reduces the desirability of such apparatus.

SUMMARY OF THE INVENTION

There is a need to have a lockable support arm that has capability for a wide range of positioning with minimal positioning limitations.

In one of its aspects, the invention provides a re-postitionable, lockable tool support apparatus including a base mount assembly, elongate first and second limb segments and tool mount means. The base joint has a rigidly interconnected pair of balls, each ball is in a ball and socket joint. The base joint is interconnected with the base mount assembly and to one end of the first limb. A rotating mid-joint interconnects the other end of said first limb to one end of said second limb. A remote joint interconnects the other end of the second limb to the instrument mount means. Each joint has releasable locking means operable between a locked position and a released position.

In another of its aspects, the invention provides a re-positionable, lockable arm-like support apparatus comprising a base including means to mount the base to a structure. The support has elongate first and second limb segments and a base joint spherically-displaceably and rotatably interconnecting said base to one end of said first limb segment. The base joint includes releasable locking means operable between a locked state where the base and the first limb segment are lockingly interconnected by the base joint. The base joint also has a released state which allows relative movement between the base and the first limb segment. The support includes a mid-joint rotatably interconnecting the other end of the first limb segment to one end of the second limb segment. The mid-joint has releasable locking means operable between a locked state, wherein the first limb segment and the second limb segment are lockingly interconnected by the mid-joint, and a released state allowing relative movement between the first limb segment and the second limb segment. The support also includes lock activation means to activate the base joint locking means and the mid-joint locking means between the locked state and the released state.

The preferred embodiment of the invention will now be described with reference to the attached figures in which:

FIG. 2 is an enlarged cross-sectional view of the base joint portion of the arm of FIG. 1.

FIG. 3 is an enlarged cross-sectional view of the mid-joint joint portion of the arm of FIG. 1.

DETAILED DESCRIPTION OF THE PREFERRED EMBODIMENT

Figure 1:
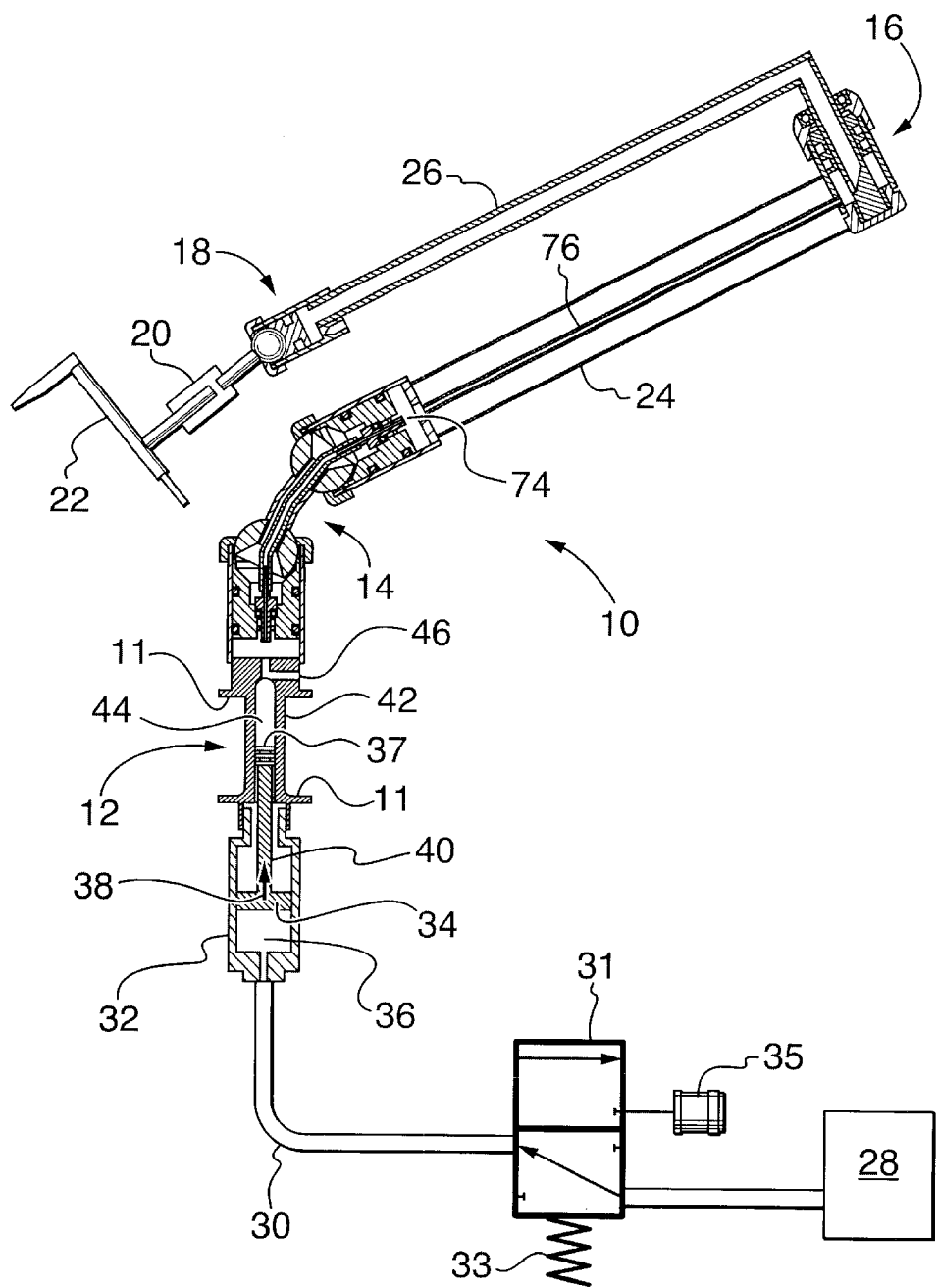
FIG. 1 is a cross-sectional elevation view of a preferred embodiment of the inventive arm.

FIG. 1 shows a partial cutaway view of a releasable lockable re-positionable arm-like support generally depicted by reference numeral 10. Arm-like apparatus 10 has a base 12 with mount means 11 for mounting the base to a support structure, such as an operating table or chair or wall or the like. Arm-like apparatus 10 also includes a base joint or shoulder joint 14, a mid-joint or elbow joint 16. Preferably arm 10 includes a remote joint or wrist joint 18. The distal end of arm 10 provides support for items to be held in position by arm-like support 10. For example, releasably coupled to wrist joint or end joint 18, is a tool mount or instrument adapter 20 provided to secure the item to be held by the distal end of arm 10. Supported by instrument adapter 20, for example, is a surgical instrument 22. In the configuration of the embodiment of the arm-like support apparatus 10 depicted in FIG. 1, surgical instrument 22 is mounted to the arm 10 after wrist joint 18 at the distal end of releasable lockable arm 10. Base joint 14 is shown in a more detailed view in FIG. 2 and mid-joint 16 is shown in a more detailed view in FIG. 3. Interconnecting base joint 14 with mid-joint 16 is a first limb segment or rigid member 24, which is preferably tubular in construction to provide a construction which is resistant to deflection and torsion forces. Extending from mid-joint 16 is a second limb segment or rigid member 26, which also is preferably tubular in construction to be resistant to deflection and torsion forces. In the configuration of the embodiment of the invention depicted in FIG. 1, arm-like support includes a remote joint or wrist joint 18.

Figure 1A:
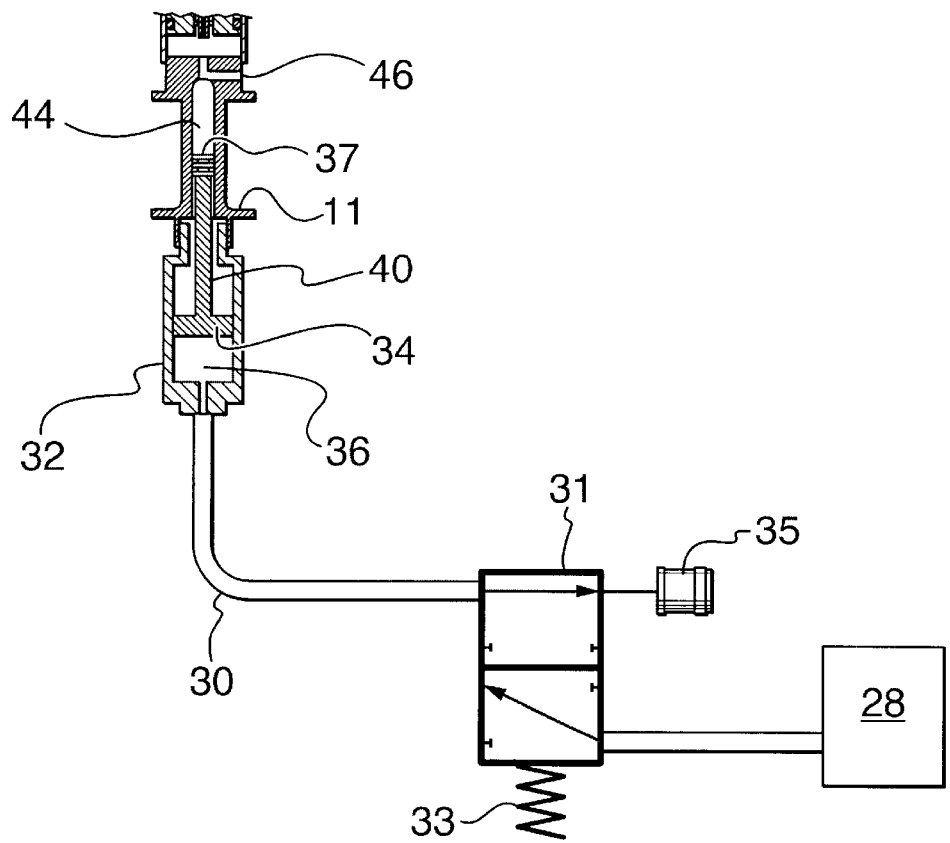
FIG. 1A is a cross-sectional elevation view of the control valve of FIG. 1 in the release position.

The releasable lockable arm 10 has a source of pressurized fluid 28 that is supplied, via supply conduit 30, to a receiving chamber 32. A control valve 31, such as a conventional pneumatic valve, controls the supply of pressurized fluid from reservoir 28 to supply conduit 30. Control valve 31 is biased into the lock configuration, to supply pressurized fluid to conduit 30, by control valve biasing means 33, which is for example a spring. The direction of flow of pressurized fluid from the source of pressurized fluid 28 depicted in schematic form by the lower, diagonal arrow of control valve 31. In this configuration, or position, of the control valve 31, releasable lockable arm 10 is locked in position. To release the arm 10 for re-positioning, control valve 31 is manipulated into the release configuration or position. FIG. 1A is a cross-sectional elevation view of the control valve 31 of FIG. 1 in the release position. In the release position, control valve 31 is manipulated by the user, such as for example by depressing a foot pedal, to reconfigure the control valve to enable supply conduit 30 to become in communication with an ambient discharge outlet 35 to discharge the pressurized fluid in supply conduit 30 and compression chamber 36 to the atmosphere. The direction of discharge fluid flow is depicted schematically by a horizontal arrow interconnecting supply conduit 30 to ambient discharge outlet 35. Ambient discharge outlet 35 preferably includes a muffler or like device to prevent unwanted discharge disturbances such as noise and gusting or puffing.

Referring again to FIG. 1, in the preferred embodiment receiving chamber 32 can include apparatus serving as a pressure amplifier. To provide a pressure amplifier, slidingly disposed within receiving chamber 32 is a piston 34. Piston 34 sealingly engages the interior surface of receiving chamber 32 to form a compression chamber 36. Pressurized fluid in compression chamber 36 acts on piston 34 to drive it axially upwardly in the direction of arrow 38. Connected to piston 34 is a compression shaft 40, the distal end of which is slidingly received by housing 42. Compression shaft 40 is in sealing engagement with housing 42 which together form a secondary fluid compression chamber 44. Preferably, the secondary fluid filling the secondary fluid compression chamber 44 is a hydraulic fluid. An increase or amplification of fluid pressure of the fluid in secondary compression chamber 44 relative to the fluid pressure of the pressurized fluid acting in compression chamber 36 can be obtained. The increase of amplification of relative fluid pressures of the chambers is obtained by providing an end surface area of piston 34 facing into compression chamber 36 which is larger than the end surface area of compression shaft 40 facing into secondary fluid compression chamber 44. Preferably a seal 37 is provided to seal compression shaft 40 in sliding engagement with secondary fluid compression chamber 44.

The housing 42 includes a secondary fluid supply passage 46 which is normally sealed but can be opened to introduce the secondary fluid such as a hydraulic fluid into the secondary fluid passages including the secondary fluid compression chamber 44. Secondary fluid supply passage 46 can also be used to bleed unwanted fluids, for example, air, from the secondary fluid side of the apparatus to ensure that there is an efficacious presence of secondary fluid within the secondary fluid system of the invention.

When the control valve 31 is manipulated into the release configuration shown in FIG. 1A, the fluid pressure in compression chamber 36 returns to atmospheric or ambient pressure. This in turn, results in removal of the force applied to compression shaft 40 and consequently ceases application of force by compression shaft 40 to the fluid contained in secondary fluid compression chamber 44. Consequently, the secondary fluid loses pressure differential relative to the ambient or atmospheric pressure releasing the lock of the joints of the arm 10 enabling the arm 10 to be positioned or re-positioned to a desired orientation.

FIG. 2 provides an enlarged cross-sectional view of the base joint 14 portion of the embodiment of the releasable lockable arm 10 of FIG. 1. The secondary fluid compression chamber 44 is in communication with a first piston chamber 48 via communicating passage 50. A piston 53 is axially, slideably displaceable within housing 52. Seals 55 maintain the integrity of the seal of piston chamber 48 with respect to housing 52. The seals 55 preferably are positioned in a seal receiving groove circumscribing piston 53 to establish a seal between piston 53 and housing 52. A first ball assembly 54 is connected to a second ball assembly 56 by means of a rigid interconnecting member 58 that prevents the relative movement of first ball assembly 54 with respect to second ball assembly 56. Provided within rigid interconnecting element 58 is a pressure supply line 60 which extends between a first rotatable sealed coupling 62 and a second rotatable sealed coupling 64. Pressure supply line 60 allows the pressurized fluid of piston chamber 48 to communicate with the second piston chamber 48a.

The upper end of housing 62 has a collar 66 securely attached thereto. Preferably collar 66 is removable from housing 52 to effect assembly and maintenance as required. For example, collar 66 may be threadingly coupled to housing 52. Collar 66 surrounds a girth of the ball of first ball assembly 54 and forms a seating surface 68 that mates with the exterior surface of the ball of first ball assembly 54. When collar 66 is secured to housing 52, the first ball assembly 54 cannot be removed from the housing 52 and collar 66 assembly as the diameter of the opening of collar 66 through which interconnecting member 58 extends is smaller than the diameter of the ball of first ball assembly 54. However, when the coupling is not in the locked position, first ball assembly 54 is free to rotate in three-dimensional space within the housing 52 and collar 66 assembly, thereby allowing the rigid interconnecting element 58 to be rotated and/or angularly displaced relative to housing 52. The displacement of the rigid interconnecting element 58 can include rotational displacement which includes rotation of the pressure supply line 60. Pressure supply line 60 is sealingly coupled within housing 52 by means of first rotatable sealed coupling 62 and seals 55. Also, when the coupling is not in a locked position, rotatable seal coupling 62 allows pressure supply line 60 to rotate within or with respect to piston 53 while maintaining a sealed relationship therewith.

For the other portion of the releasable lockable joint, one end of housing 52a has a collar 66a securely attached thereto. Preferably collar 66a is removable from housing 52a to effect assembly and maintenance as required. For example, collar 66a may be threadingly coupled to housing 52a. Collar 66a surrounds a girth of the ball of the second ball assembly 56 and forms a seating surface 68a that mates with the exterior surface of second ball assembly 56. When collar 66a is secured to housing 52a, the second ball assembly 56 cannot be removed from the housing 52a and collar 66a assembly as the diameter of the opening of collar 66a through which interconnecting member 58 extends is smaller than the diameter of the ball of second ball assembly 56. However, when the coupling is not in the locked position, second ball assembly 56 is free to rotate in three-dimensional space within the housing 52a and collar 66a assembly, thereby allowing the rigid interconnecting element 58 to be rotated and/or angularly displaced relative to housing 52a. The displacement of the rigid interconnecting element 58 can include rotational displacement which includes rotation of the pressure supply line 60 with respect to piston 53a. Pressure supply line 60 is sealingly coupled within housing 52a by means of second rotatable sealed coupling 64 and seals 55a. Also, when the coupling is not in a locked position, rotatable seal coupling 64 allows pressure supply line 60 to rotate within or with respect to piston 53a while maintaining a sealed relationship therewith.

Because of communicating pressure line 60, pressurized fluid supplied from the fluid compression chamber 44 is supplied to piston chambers 48 and 48a simultaneously. To lock first ball assembly 54 with respect to housing 52, a pressurized fluid, such as hydraulic fluid, is supplied to piston chamber 48. The pressurized fluid applies a force to the area of piston 53 to urge upwardly on piston 53 in the direction of arrows 70. As a consequence of such force, piston 53 is urged to travel upwardly until seat 72 engages first ball assembly 54 thereby compressing the ball assembly 54 between seat 72 and seating surface 68 of collar 66. When this compression seating occurs, first ball assembly 54 is maintained in a locked configuration with respect to housing 52 thereby preventing any relative movement therebetween. In the locked configuration, interconnecting element 58 cannot move relative to housing 52.

Simultaneously with the action of the pressurized fluid causing piston 53 to be urged in the direction of arrows 70, the communicating passageway, established by first rotatable seal coupling 62, pressure supply line 60 and second rotatable seal coupling 64, extending to second piston chamber 48a, causes pressurized fluid also to be supplied to second piston chamber 48a. The pressurized fluid produces a force against the surface area of piston 53a causing it to be urged to move in the direction of arrow 70a thereby to urge seat 72a toward seat 68a and, consequently, compressing second ball assembly 56 therebetween. When second ball assembly 56 is compressed between seats 72a and 68a, it is rigidly held in position relative to housing 52a. Thus, the supply of a pressurized fluid from the secondary compression chamber 44 causes base joint 14 to become locked in position. The pressurized fluid is communicated to egress passage 74 to permit the pressurized fluid to be transmitted externally to base joint 14. In FIG. 1, pressurized supply tube 76 carries the fluid from egress passage 74 to mid-joint 16. Mid-joint 16 is shown in enlarged view in FIG. 3.

FIG. 3 shows, in partial cut away or cross sectional view, a second rigid member 26 which is rotatably connected to first rigid member 24 through mid-joint 16. Mid-joint 16 has a housing 78 forming a pressure chamber 80. Pressure chamber 80 is in communication with supply tube 76. Affixed to second rigid member 26 is a sleeve 82 rotatably disposed within pressure chamber 80. Sleeve 82 is preferably rigidly connected to second rigid member 26, for example, by welding to prevent axial rotational movement therebetween. Housing 78 has an upper collar 84 which forms a seat 86 in the interior thereof. Upper collar 84 rotatably receives second rigid member 26, preferably by means of a roller bearing assembly 88 extending therebetween. When the fluid contained within pressure chamber 80 becomes pressurized, sleeve 82 is urged upwardly in direction of arrows 90. When sleeve 82 is urged upwardly, the upper mating surface of sleeve 82 contacts with seat 86 thereby preventing relative movement between sleeve 82 and seat 86. Because sleeve 82 is rigidly connected to second rigid member 26 and seat 86 is stationary with respect to housing 78 and first rigid member 24, the mating engagement of sleeve 82 with seat 86 prevents the relative rotational movement of second rigid member 26 with respect to first rigid member 24. Conversely, when the pressure is removed from the fluid filling the pressure chamber 80, the upper mating surface of sleeve 82 is no longer forced into contact with seat 86 thereby allowing relative movement of second rigid member 26 with respect to first rigid member 24. To maintain the integrity of the seal of the pressure chamber 80, seals 81 are preferably indicated.

A passageway 92 is in communication with pressure chamber 80 to allow pressurized fluid to be delivered to wrist joint 18 through a pressure supply line formed by the interior hollow portion of second rigid member 26. The wrist joint 18 is preferably a lockable ball joint assembly constructed and operated in a similar fashion and manner as was described in relation to each of the pair of ball joints forming base joint 14 and shown in enlarged view in FIG. 2.

Figure 4:
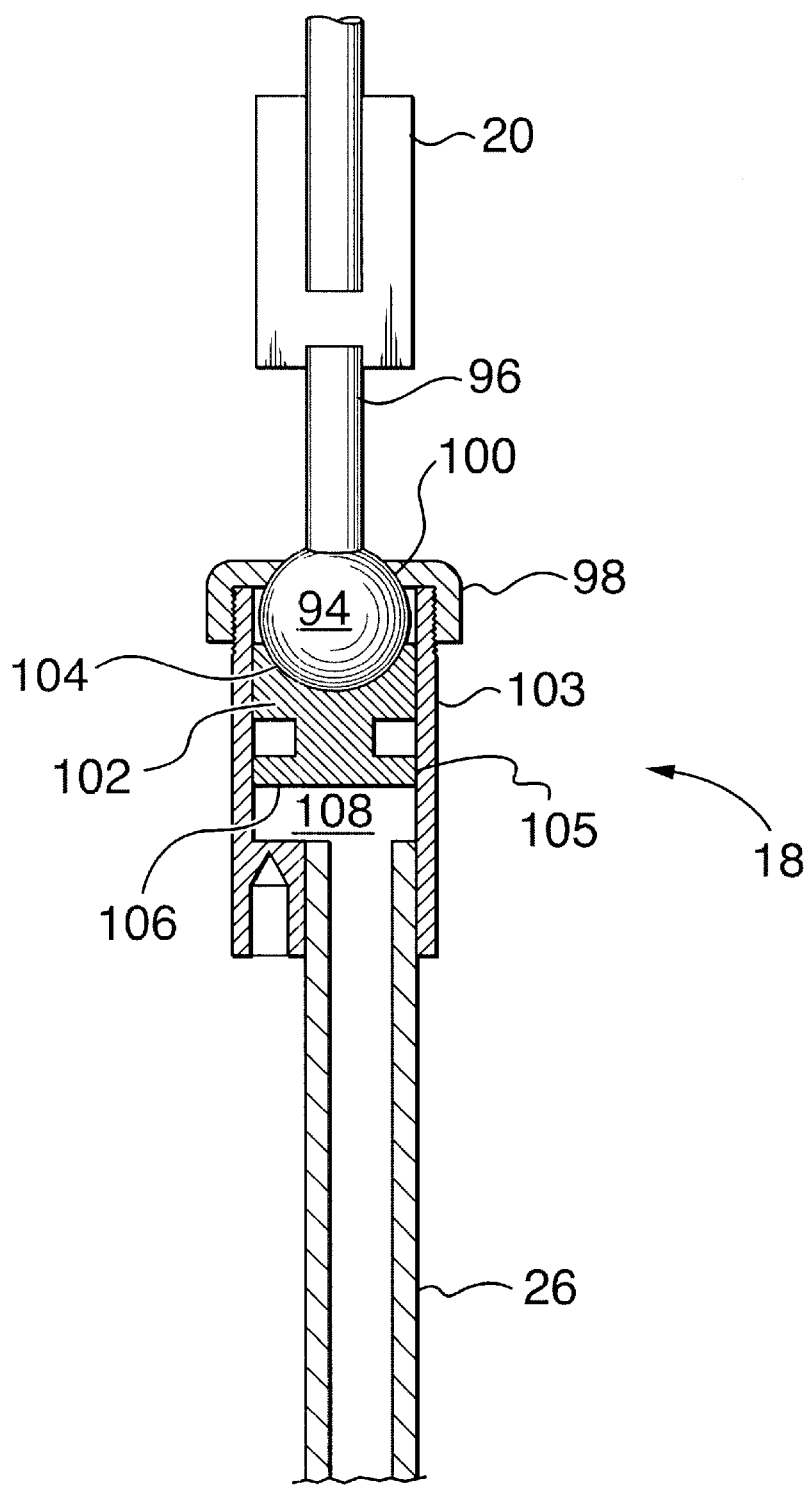
FIG. 4 is an enlarged cross-sectional view of the end joint portion of the arm of FIG. 1.

FIG. 4 shows an enlarged cross-sectional view of the end joint portion of the arm of FIG. 1. End joint or wrist joint 18 has a ball 94 including a mount adapter 96 extending therefrom through collar 98. Collar 98 forms a seat 100 in the interior portion of joint 18, the seat dimensioned to surround a girth of ball 94. On the other side of ball 94 from collar seat 100 is piston 102. One end of piston 102 forms a seat 104 dimensioned to seat with ball 94. Piston 102 is slideably received in housing 103 of end joint 18. Preferably, a seal 105 surrounds piston 102 to prevent escape of pressurized fluid from chamber 108. The end of piston 102 opposite seat 104 forms a surface 108 on which pressure exerted by fluid contained in chamber 108 will cause a force to be produced to urge piston seat 104 toward collar seat 100 to grippingly engage ball 94 therebetween. Increasing pressure of the fluid in chamber 108 will cause joint 18 to become in a locked state due to increasing frictional engagement of seats 100, 104 to ball 94. In the locked state, joint ball 94 is prevented from moving with respect to joint housing 103, consequently preventing any relative movement between mount adapter 96 with respect to arm second rigid member 26. Conversely, decreasing pressure of the fluid in chamber 108 will relax the grip of seats 100, 104 on ball 94 enabling ball 94 of joint 18 to become released, consequently permitting mount adapter 96 to be rotated with respect to arm second rigid member 26 as well as angularly displaced with respect thereto. Preferably, second rigid member 26 is hollow to permit the pressurized fluid applied to the arm from pressure chamber 44 to be communicated to end joint 18 through 60, 48a, 74, 76, 80 and 92 on its way to 26 to supply joint 18. Alternately, second rigid member 26 can carry a pressure tube supply line (not shown) to communicate fluid pressure to end joint 18.

Figure 5:
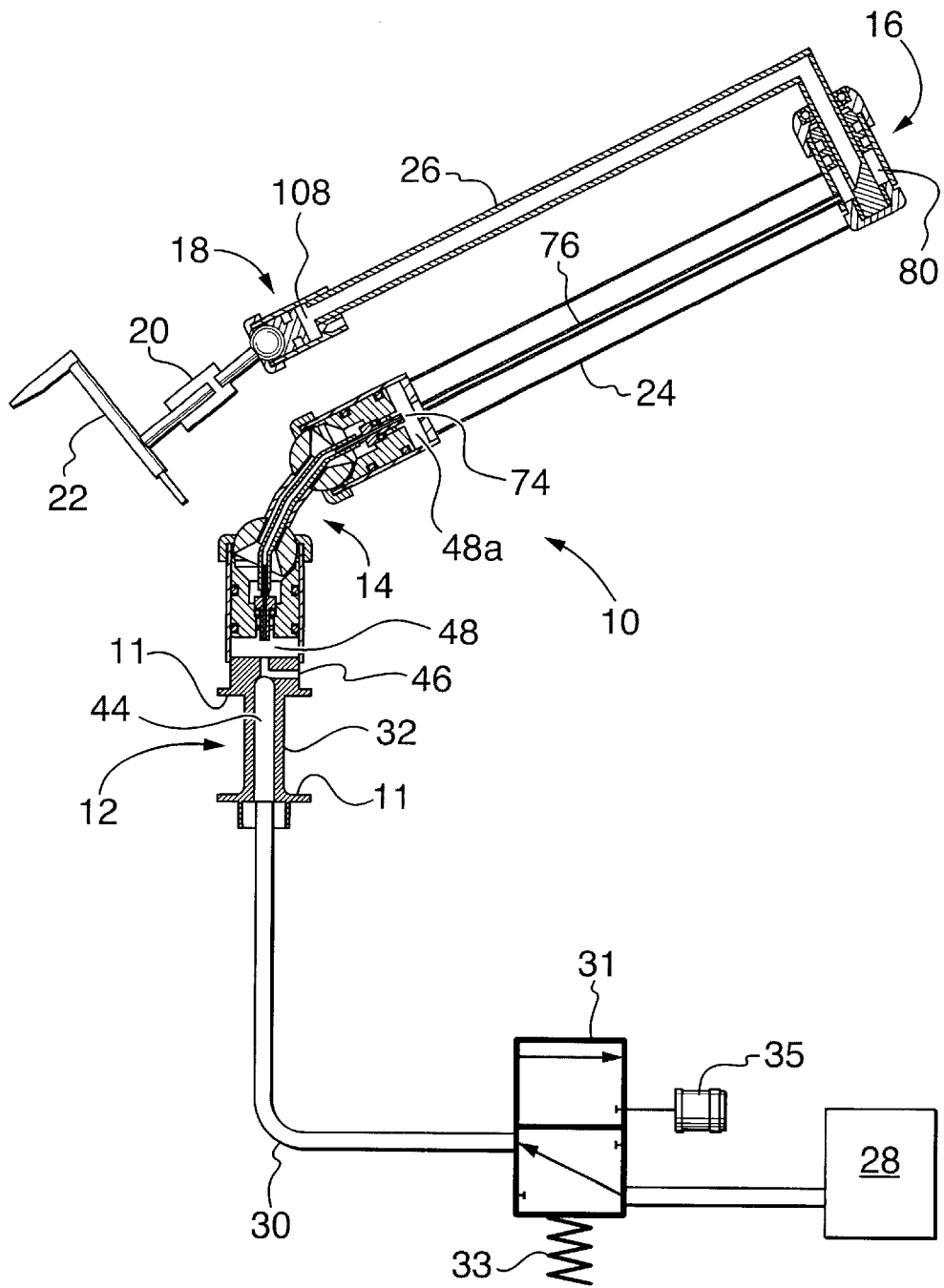
FIG. 5 is a cross-sectional elevation view of another embodiment of the inventive arm.

FIG. 5 shows a partial cutaway or cross section view of another embodiment of arm support 10. In this embodiment, a source of pressurized fluid 28 is supplied via control valve 31 to supply conduit 30 to a receiving chamber 32. The control valve 31 is a conventional pneumatic valve, in the embodiment shown. As will be understood by those skilled in the art, a hydraulic valve may also be used, with suitable modification to the ambient discharge 35 to enable hydraulic fluid venting to be returned to a hydraulic reservoir (not shown). From receiving chamber 32, the pressure of the fluid in supply conduit 30 is carried to other areas of the arm 10 to activate and control the locking and releasing of the joints of the arm 10. That is the fluid pressure of supply conduit 30 is communicated to piston chambers 48 and 48a of base joint 14 and along supply tube 76 to pressure chamber 80 of mid joint 16 and also along the arm second rigid member 26 to supply pressure to chamber 108 of end joint 108. When the pressure of the fluid in supply conduit 30 is increased, the joints 14, 16 and 18 will become locked thereby preventing relative movement of the elements of the arm 10. When the pressure of the fluid in supply conduit 30 is decreased, the joints 14, 16 and 18 will become released thereby permitting relative movement of the elements of the arm 10. The pressure of the fluid in supply conduit 30 is controlled by manipulation of control valve 31, which, in turn, controls the locked and released state of arm 10.

Now that the invention has been described with reference to the attached drawings, numerous substitutions, modifications and equivalents will occur to those skilled in the art. The invention is defined by the claims appended hereto.

The embodiments of the invention in which an exclusive property or privilege is claimed are as follows:

1. A re-positionable, lockable arm-like support apparatus comprising:
   a) a base including means to mount said base to a structure;
   b) elongate first and second limb segments;
   c) a base joint spherically-displaceably and rotatably interconnecting said base to one end of said first limb segment;
   d) base joint releasable locking means operable between a locked state wherein said base and said first limb segment are lockingly interconnected by said base joint and a released state allowing relative movement between said base and said first limb segment;
   e) a mid-joint rotatably interconnecting the other end of said first limb segment to one end of said second limb segment;
   f) mid-joint releasable locking means operable between a locked state wherein said first limb segment and said second limb segment are lockingly interconnected by said mid-joint and a released stab allowing relative movement between said first limb segment and said second limb segment;
   g) lock activation means to activate said base joint locking means and said mid joint locking means between said locked state and said released state comprising a piston chamber for applying compression forces to a fluid in communication with said base joint releasable locking means and said mid-joint releasable locking means.

2. The apparatus of claim 1 wherein said base joint comprises a rigidly interconnected pair of ball and socket joints.

3. The apparatus of claim 2 wherein each said ball and socket joint of said base joint releasable locking means comprises:
   a) a housing;
   b) a collar disposed on one side of said housing forming a seat to surround a girth of a ball; and
   c) a piston slidingly disposed within said housing, one end thereof including a seat adapted for mating engagement with said ball and the other end of said piston forming a chamber within said housing.

4. The apparatus of claim 1 further including:
   a) means for mounting a tool;
   b) an end joint interconnecting said means for mounting a tool to the other end of said second limb segment; and
   c) end joint releasable locking means operable between a locked state wherein said tool mount means and said second limb segment are lockingly interconnected by said end joint and a released state allowing relative movement between said tool mount means and said second limb segment.

5. The apparatus of claim 4 wherein said end joint spherically-displaceably and rotatably interconnects said means for mounting a tool to said second limb segment.

6. The apparatus of claim 1 wherein said releasable locking means are operable between said locked state and said released state responsive to the supply of a pressurized fluid.

7. The apparatus of claim 6 wherein said lock activation means comprises:
   a) a supply conduit operable to supply pressurized fluid to activate each said releasable locking means;
   b) a source of pressurized fluid;
   c) a control valve operable between a locking configuration connecting said source of pressurized fluid to said supply conduit and a releasing configuration whereby said base joint locking means and said mid joint locking means enter said locked state and said released state in response to the configuration of said control valve.

8. The apparatus of claim 7 further including pressure amplification means comprising:
   a) a housing forming a first receiving chamber in fluid communication with said supply conduit;
   b) a piston slidingly disposed in said housing to form a first fluid compression chamber;
   c) a second housing slidingly receiving a compression shaft therein forming second fluid compression chamber, said compression shaft coupled to said piston; wherein the surface area of said compression shaft facing into said second fluid compression chamber is less than the surface area of said piston facing into said first fluid compression chamber.

* * * * *